(12) United States Patent
Scates et al.

(10) Patent No.: US 9,302,969 B1
(45) Date of Patent: Apr. 5, 2016

(54) PROCESSES FOR PRODUCING ACETIC ACID BY INTRODUCING A LITHIUM COMPOUND

(71) Applicant: Celanese International Corporation, Irving, TX (US)

(72) Inventors: Mark O. Scates, Houston, TX (US); Yaw-Hwa Liu, Missouri City, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days.

(21) Appl. No.: 14/874,213

(22) Filed: Oct. 2, 2015

Related U.S. Application Data

(60) Provisional application No. 62/080,035, filed on Nov. 14, 2014.

(51) Int. Cl.
*C07C 51/12* (2006.01)

(52) U.S. Cl.
CPC ..................................... *C07C 51/12* (2013.01)

(58) Field of Classification Search
CPC .................................................... A01B 12/006
See application file for complete search history.

(56) References Cited

U.S. PATENT DOCUMENTS

| | | | |
|---|---|---|---|
| 4,302,432 | A | 11/1981 | Polichnowski |
| 4,733,006 | A | 3/1988 | Singleton et al. |
| 4,792,620 | A | 12/1988 | Paulik et al. |
| 5,001,259 | A | 3/1991 | Smith et al. |
| 5,026,908 | A | 6/1991 | Smith et al. |
| 5,144,068 | A | 9/1992 | Smith et al. |
| 6,303,813 | B1 | 10/2001 | Scates et al. |
| 6,323,364 | B1 | 11/2001 | Agrawal et al. |
| 7,342,129 | B2 | 3/2008 | Law et al. |
| 7,476,761 | B2 | 1/2009 | Kojima |
| 8,168,822 | B2 | 5/2012 | Scates |
| 8,940,932 | B2 | 1/2015 | Shimizu |
| 8,957,248 | B2 | 2/2015 | Miura et al. |
| 9,006,483 | B2 | 4/2015 | Shimizu et al. |
| 9,073,843 | B2 | 7/2015 | Shimizu et al. |
| 9,115,071 | B2 | 8/2015 | Shimizu et al. |
| 2013/0264186 | A1 | 10/2013 | Shimizu et al. |
| 2013/0281735 | A1 | 10/2013 | Shimizu et al. |

FOREIGN PATENT DOCUMENTS

| | | |
|---|---|---|
| CN | 104689854 A | 6/2015 |
| EP | 0 161 874 A1 | 11/1985 |
| WO | 2014/115826 A1 | 7/2014 |

OTHER PUBLICATIONS

Smith et al. (The Rhodium-Catalyzed Methanol Carbonylation to Acetic Acid at Low Water Concentrations: The Effect of Iodide and Acetate on Catalyst Activity and Stability, Journal of Molecular Catalysis, 39, 115-136, 1987).*
Office Action Cited in U.S. Appl. No. 14/874,332, dated Jan. 6, 2016, 15 pages.
Haynes, A. (2010). "Catalytic Methanol Carbonylation," *Advances in Catalysis* 53:1-45.
Haynes, A. (2006, e-pub. May 25, 2006). "Acetic Acid Synthesis by Catalytic Carbonylation of Methanol," *in* Topics in Organometallic Chemistry, Catalytic Carbonylation Reactions, Springer-Verlag, Berlin, Heidelberg, 18:179-205.
Jones, J.H. (2000). "The Cativa$^{SM}$ Process for the Manufacture of Acetic Acid," *Platinum Metals Review* 44(3):94-105.
Smith, B.L. et al. (1987). "The Rhodium-Catalyzed Methanol Carbonylation to Acetic Acid at Low Water Concentrations: The Effect of Iodide and Acetate on Catalyst Activity and Stability," *Journal of Molecular Catalysis* 39:115-136.
International Search Report receive d in the corresponding PCT Application No. PCT/US2015/053839, dated Jan. 21, 2016, 46 pgs.

* cited by examiner

*Primary Examiner* — Yevegeny Valenrod
*Assistant Examiner* — Blaine G Doletski
(74) *Attorney, Agent, or Firm* — Kilpatrick Townsend & Stockton LLP

(57) ABSTRACT

Process for producing acetic acid is disclosed in which a lithium compound is added to the reaction medium to maintain a concentration of lithium acetate from 0.3 to 0.7 wt. %. The concentration of the rhodium catalyst is maintained from 300 to 3000 wppm in the reaction medium, the concentration of water is maintained from 0.1 to 4.1 wt. % in the reaction medium, and the concentration of methyl acetate is maintained from 0.6 to 4.1 wt. % in the reaction medium.

20 Claims, 4 Drawing Sheets

PROCESSES FOR PRODUCING ACETIC ACID BY INTRODUCING A LITHIUM COMPOUND

CROSS-REFERENCES TO RELATED APPLICATIONS

This patent application claims priority from U.S. Provisional Application Ser. No. 62/080,035, entitled "Processes For Producing Acetic Acid by Introducing a Lithium Compound," filed Nov. 14, 2014, the disclosure of which is incorporated herein by reference in its entirety.

FIELD OF THE INVENTION

This invention relates to processes for producing acetic acid and, in particular, to improved processes for introducing a lithium compound into the reaction medium to control hydrogen iodide formation.

BACKGROUND OF THE INVENTION

Among currently employed processes for synthesizing acetic acid, one of the most useful commercially is the catalyzed carbonylation of methanol with carbon monoxide as taught in U.S. Pat. No. 3,769,329, which is incorporated herein by reference in its entirety. The carbonylation catalyst contains a Group VIII metal catalyst, such as rhodium, which is either dissolved or otherwise dispersed in a liquid reaction medium or supported on an inert solid, along with a halogen-containing catalyst promoter as exemplified by methyl iodide. Most typically and usefully, the reaction is conducted by continuously bubbling carbon monoxide gas through a liquid reaction medium in which the catalyst is dissolved. The production of acetic acid by the carbonylation of methanol requires the use of large amounts of iodide compounds in the reaction medium. The composition of the reaction medium is a key aspect for efficiently producing acetic acid, stabilizing the rhodium catalyst, and reducing byproduct formation. In particular, the formation of byproducts such as hydrogen iodide that promote water gas shift reactions and increase corrosion should be reduced.

Haynes (2010) "Catalystic Methanol Carbonylation," reports that raising methyl acetate concentration results in lower hydrogen iodide concentration, which tends to inhibit oxidation of $[Rh(CO)_2I_2]^-$ to give $[Rh(CO_2)_2I_4]^-$, thus suppressing the water gas shift reaction significantly.

U.S. Pub. No. 2013/0310603 discloses an acetic acid production process comprising a reaction step for continuously allowing methanol to react with carbon monoxide in the presence of a catalyst system comprising a metal catalyst (e.g., a rhodium catalyst), an ionic iodide (e.g., lithium iodide), and methyl iodide in a carbonylation reactor; and in the process, (i) the concentration of the metal catalyst is maintained at not less than 860 ppm on the basis of weight, the concentration of water is maintained at 0.8 to 15% by weight, the concentration of methyl iodide is maintained at not more than 13.9% by weight, and the concentration of methyl acetate is maintained at not less than 0.1% by weight, in a whole liquid phase in the reactor, and/or (ii) the concentration of the metal catalyst is maintained at not less than 660 ppm on the basis of weight, the concentration of water is maintained at 0.8 to 3.9% by weight, the concentration of the ionic iodide is maintained at not more than 13% by weight, the concentration of methyl iodide is maintained at not more than 13.9% by weight, and the concentration of methyl acetate is maintained at not less than 0.1% by weight, in a whole liquid phase in the reactor. Many others such as U.S. Pat. Nos. 4,994,608; 6,211,405; 6,657,078; 7,005,541; 7,476,761; and 7,884,241 have described overlapping component ranges in the reaction medium. U.S. Pat. App. Pub. No. 2013/0310603 claims that a reaction medium having these concentrations inhibits an increase in concentration of hydrogen iodide in the carbonylation reactor.

U.S. Pat. No. 4,733,006 discloses a process wherein an olefin, an alcohol, or an ester, halide or ether derivative of said alcohol is reacted with carbon monoxide in a liquid phase in the presence of a catalyst system that contains (a) a rhodium component, and (b) an iodide or bromine component. By passing at least a portion of the liquid reaction mass from the reaction zone to a separation zone of substantially lower CO partial pressure, at least a portion of the carbonylation products, as well as unreacted carbon monoxide, inert gases and unreacted olefin, alcohol, or alcohol derivatives are vaporized and can be withdrawn from the separation zone. Precipitation of the rhodium catalyst under carbon monoxide deficient conditions is prevented or retarded by addition to the carbon monoxide deficient zones of the system of a catalyst stabilizer which is a germanium (IV) compound, an alkali metal compound, and mixtures thereof. The alkali metal compound may include lithium acetate.

U.S. Pat. No. 5,001,259 discloses methanol that is reacted with carbon monoxide in a liquid reaction medium containing a rhodium catalyst stabilized with an iodide salt, especially lithium iodide, along with alkyl iodide such as methyl iodide and alkyl acetate such as methyl acetate in specified proportions. U.S. Pat. No. 5,001,259 deals with the equilibrium existing in the reaction medium between lithium iodide and lithium acetate: $LiI+MeOAc \leftrightarrow LiOAc+MeI$. With decreasing water content the lithium acetate content of the reaction medium increases, this effect being greater when 12 wt. % methyl acetate is present as compared with 4 wt. %. U.S. Pat. No. 5,001,259 reports that this equilibration between lithium iodide and lithium acetate which is dependent on the water concentration of the reaction medium has been found, incidentally, to have no adverse effect on the behavior of the catalyst system. This equilibrium will allow the increasing of the lithium iodide concentration of the reaction medium by adding, if desired, lithium acetate or other lithium salts. Because of this equilibrium, one cannot distinguish the effect of lithium iodide from that of lithium acetate on the reaction rate, and it is possible that both the lithium iodide and lithium acetate increase the reaction rate, especially with catalyst solutions with low water concentration. Adding either lithium acetate or lithium iodide allows one to eventually obtain the same equilibrium mixture of both salts in solution.

U.S. Pat. No. 8,168,822 discloses a method of making acetic acid that includes: (a) catalytically reacting methanol or a reactive derivative thereof with carbon monoxide in the presence of a homogeneous Group VIII metal catalyst and a methyl iodide promoter in a reactor vessel in a liquid reaction mixture including acetic acid, water, methyl acetate, methyl iodide and homogeneous catalyst, the reactor vessel being operated at a reactor pressure; (b) withdrawing reaction mixture from the reaction vessel and feeding the withdrawn reaction mixture along with additional carbon monoxide to a pre-flasher/post-reactor vessel operated at a pressure below the reactor vessel pressure; (c) venting light ends in the pre-flasher vessel and concurrently consuming methyl acetate in the pre-flasher/post-reactor vessel. Iodide salt stabilizer/co-promoters may be in the form of a soluble salt of an alkali metal or alkaline earth metal or a quaternary ammonium or phosphonium salt, and in particular lithium iodide, lithium acetate, or mixtures thereof.

Under anhydrous conditions, U.S. Pat. No. 4,302,432 discloses a process for the preparation of hydrogen iodide, lithium iodide, and methyl iodide by the reaction of hydrogen and iodide in a non-alcoholic solvent using a homogeneous rhodium catalyst. Lithium iodide and/or methyl iodide are obtained by including lithium acetate and/or methyl acetate in the reaction medium.

In view of the foregoing, the need exists for an improved reaction medium to produce acetic acid with commercially acceptable yields and with low by-product formation.

SUMMARY OF THE INVENTION

In one embodiment, the present invention relates to a process for producing acetic acid comprising carbonylating a reactant feed stream comprising methanol, methyl acetate, dimethyl ether, or mixtures thereof in a reactor in the presence of water, rhodium catalyst, iodide salt, and methyl iodide to form a reaction medium; introducing a lithium compound into the reactor; and maintaining a concentration of lithium acetate in the reaction medium from 0.3 to 0.7 wt. %, e.g., from 0.3 to 0.6 wt. %, and the concentration of hydrogen iodide in the reaction medium from 0.1 to 1.3 wt. %, e.g., from 0.1 to 1 wt. % or from 0.2 to 0.8 wt. %, wherein the concentration of the rhodium catalyst in the reaction medium is maintained from 300 to 3000 wppm, as rhodium, the concentration of water in the reaction medium is maintained from 0.1 to 4.1 wt. %, and the concentration of methyl acetate in the reaction medium is maintained from 0.6 to 4.1 wt. %. The lithium compound may be selected from the group consisting of lithium acetates, lithium carboxylates, lithium carbonates, lithium hydroxides, and mixtures thereof.

The reaction medium may comprise methyl iodide, and in one embodiment, the concentration of methyl iodide in the reaction medium is maintained from 4 to 13.9 wt. %, preferably from 4 to 13 wt. %. The reaction medium may comprise an iodide salt, such as lithium iodide, and in one embodiment, the concentration of iodide salt in the reaction medium is maintained from 2 to 20 wt. %, preferably from 8 to 14 wt. %. The weight ratio of iodide salt to lithium compound is greater than or equal to 5:1. In addition, the concentration of methyl acetate in the reaction medium is greater than or equal to the concentration of the lithium acetate. The reaction is conducted while maintaining a carbon monoxide partial pressure from 2 to 30 atm and a hydrogen partial pressure of less than or equal to 0.04 atm in the reactor. The reaction may also be conducted at a temperature from 150° C. to 250° C. and at a pressure from 15 to 40 atm.

In another embodiment, in the reaction medium, the concentration of lithium acetate is maintained from 0.3 to 0.6 wt. %, the concentration of the rhodium catalyst is maintained from 800 to 3000 wppm, the concentration of water is maintained from 0.1 to 3.1 wt. %, the concentration of methyl acetate is maintained from 1.8 to 3.9 wt. %, and the concentration of hydrogen iodide is maintained from 0.1 to 1 wt. %.

In another embodiment, in the reaction medium, the concentration of lithium acetate is maintained from 0.35 to 0.55 wt. %, the concentration of the rhodium catalyst is maintained from 900 to 1500 wppm, the concentration of water is maintained from 0.5 to 2.8 wt. %, the concentration of methyl acetate is maintained from 2 to 3.5 wt. %, and the concentration of hydrogen iodide is maintained from 0.2 to 0.8 wt. %.

In another embodiment, the production rate of acetic acid is from 10 mol/L·h to 40 mol/L·h and wherein in the reaction medium, the concentration of lithium acetate is maintained from 0.3 to 0.6 wt. %, the concentration of the rhodium catalyst is maintained from 800 to 3000 wppm, the concentration of water is maintained from 0.1 to 3.1 wt. %, the concentration of methyl acetate is maintained from 1.8 to 3.9 wt. %, and the concentration of hydrogen iodide is maintained from 0.1 to 1 wt. %.

In another embodiment, the production rate of acetic acid is from 15 mol/L·h to 35 mol/L·h and wherein in the reaction medium, the concentration of lithium acetate is maintained from 0.35 to 0.55 wt. %, the concentration of the rhodium catalyst is maintained from 900 to 1500 wppm, the concentration of water is maintained from 0.5 to 2.8 wt. %, the concentration of methyl acetate is maintained from 2 to 3.5 wt. %, and the concentration of hydrogen iodide is maintained from 0.2 to 0.8 wt. %.

In a further embodiment, the present invention is directed to process for producing acetic acid comprising carbonylating a reactant feed stream comprising methanol, methyl acetate, dimethyl ether, or mixtures thereof in a reactor in the presence of water, rhodium catalyst, iodide salt, and methyl iodide to form a reaction medium, wherein the concentration of water in the reaction medium is maintained from 0.1 to 4.1 wt. %; introducing a lithium compound into the reactor; maintaining a concentration of lithium acetate in the reaction medium from 0.3 to 0.7 wt. %; venting a gaseous stream from the reactor, wherein the gaseous stream comprises hydrogen iodide in an amount of less than or equal to 1 wt. %; and recovering acetic acid from the reaction medium. In one embodiment, the gaseous stream comprises hydrogen iodide in an amount from 0.001 to 1 wt. %. The concentration of the rhodium catalyst in the reaction medium may be maintained from 300 to 3000 wppm, as rhodium, the concentration of water in the reaction medium may be maintained from 0.1 to 4.1 wt. %, and the concentration of methyl acetate in the reaction medium may be maintained from 0.6 to 4.1 wt. %. This further embodiment may also comprise scrubbing the gaseous stream to remove hydrogen iodide from a purge stream.

BRIEF DESCRIPTION OF THE DRAWINGS

The present invention will be better understood in view of the appended non-limiting figures, wherein.

DETAILED DESCRIPTION OF THE INVENTION

Figure 1:
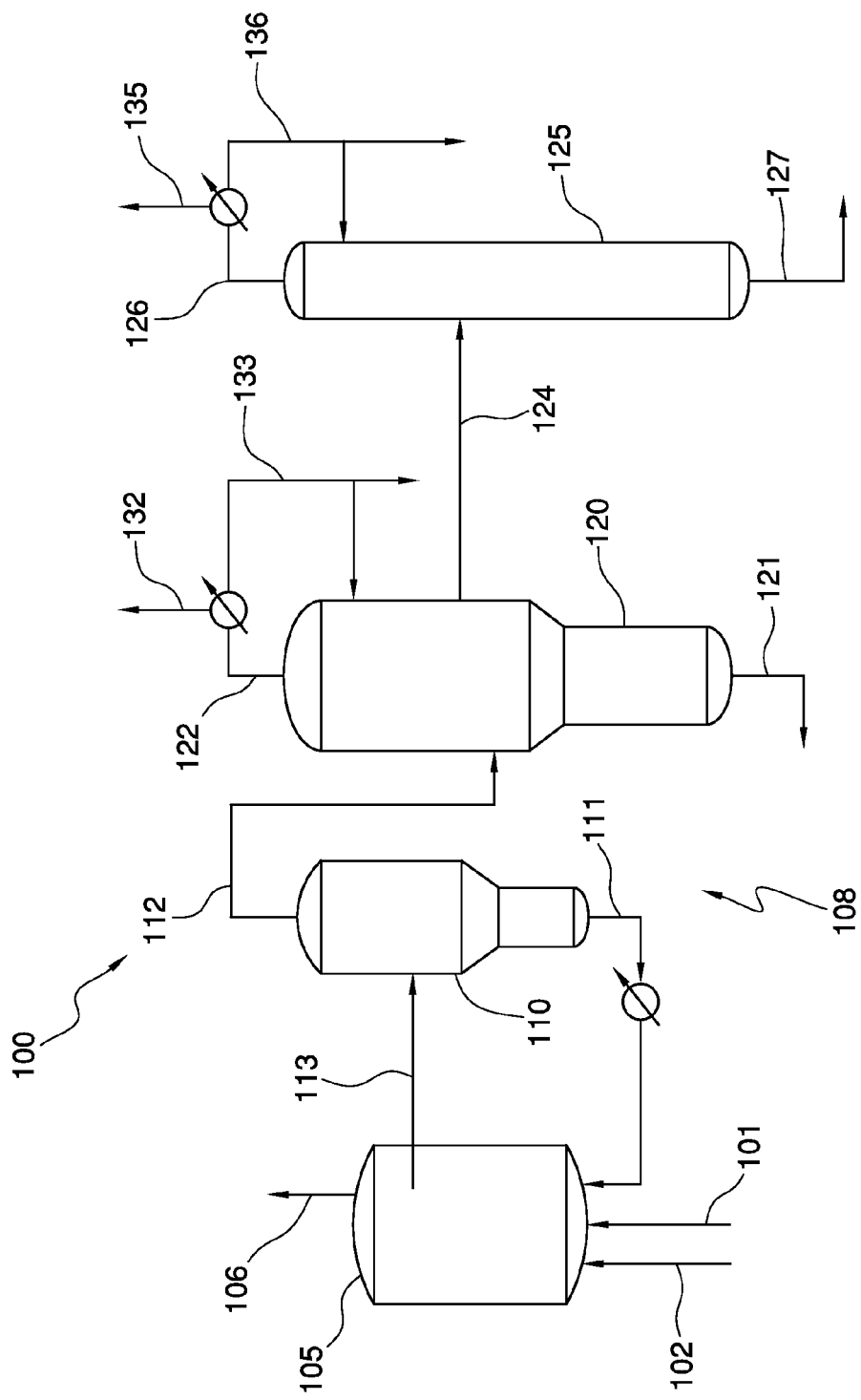
FIG. 1 is a schematic drawing of an acetic acid production process in accordance with an embodiment of the present invention.

At the outset, it should be noted that in the development of any such actual embodiment, numerous implementation-specific decisions must be made to achieve the developer's specific goals, such as compliance with system-related and business-related constraints, which will vary from one implementation to another. In addition, the processes disclosed herein can also comprise components other than those cited or specifically referred to, as is apparent to one having average or reasonable skill in the art.

In the summary and this detailed description, each numerical value should be read once as modified by the term "about"

(unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, a range "from 1 to 10" is to be read as indicating each and every possible number along the continuum between about 1 and about 10. Thus, even if specific data points within the range, or even no data points within the range, are explicitly identified or refer to only a few specific data points, it is to be understood that inventors appreciate and understand that any and all data points within the range are to be considered to have been specified, and that inventors possessed knowledge of the entire range and all points within the range.

Throughout the entire specification, including the claims, the following terms have the indicated meanings unless otherwise specified.

As used in the specification and claims, "near" is inclusive of "at." The term "and/or" refers to both the inclusive "and" case and the exclusive "or" case, and is used herein for brevity. For example, a mixture comprising acetic acid and/or methyl acetate may comprise acetic acid alone, methyl acetate alone, or both acetic acid and methyl acetate.

All percentages are expressed as weight percent (wt. %), based on the total weight of the particular stream or composition present, unless otherwise noted. Room temperature is 25° C. and atmospheric pressure is 101.325 kPa unless otherwise noted.

For purposes herein:
acetic acid may be abbreviated as "AcOH";
acetaldehyde may be abbreviated as "AcH";
methyl acetate may be abbreviated "MeAc";
methanol may be abbreviated "MeOH";
methyl iodide may be abbreviated as "MeI";
hydrogen iodide may be abbreviated as "HI";
carbon monoxide may be abbreviated "CO"; and
dimethyl ether may be abbreviated "DME".

HI refers to either molecular hydrogen iodide or dissociated hydriodic acid when at least partially ionized in a polar medium, typically a medium comprising at least some water. Unless otherwise specified, the two are referred to interchangeably. Unless otherwise specified, HI concentration is determined via acid-base titration using a potentiometric end point. In particular, HI concentration is determined via titration with a standard lithium acetate solution to a potentiometric end point. It is to be understood that for purposes herein, the concentration of HI is not determined by subtracting a concentration of iodide assumed to be associated with a measurement of corrosion metals or other non H+ cations from the total ionic iodide present in a sample.

It is to be understood that HI concentration does not refer to iodide ion concentration. HI concentration specifically refers to HI concentration as determined via potentiometric titration.

This subtraction method is an unreliable and imprecise method to determine relatively lower HI concentrations (i.e., less than or equal to about 5 weight percent) due to the fact that it assumes all non-H+ cations (such as cations of Fe, Ni, Cr, Mo) are associated with iodide anion exclusively. In reality, a significant portion of the metal cations in this process can be associated with acetate anion. Additionally, many of these metal cations have multiple valence states, which adds even more unreliability to the assumption on the amount of iodide anion which could be associated with these metals. Ultimately, this method gives rise to an unreliable determination of the actual HI concentration, especially in view of the ability to perform a simple titration directly representative of the HI concentration.

For purposes herein, an "overhead" or "distillate" of a distillation column refers to at least one of the lower boiling condensable fractions which exits at or near the top, (e.g., proximate to the top), of the distillation column, and/or the condensed form of that stream or composition. Obviously, all fractions are ultimately condensable, yet for purposes herein, a condensable fraction is condensable under the conditions present in the process as readily understood by one of skill in the art. Examples of noncondensable fractions may include nitrogen, hydrogen, and the like. Likewise, an overhead stream may be taken just below the upper most exit of a distillation column, for example, wherein the lowest boiling fraction is a non-condensable stream or represents a de-minimis stream, as would be readily understood by one of reasonable skill in the art.

The "bottoms" or "residuum" of a distillation column refers to one or more of the highest boiling fractions which exit at or near the bottom of the distillation column, also referred to herein as flowing from the bottom sump of the column. It is to be understood that a residuum may be taken from just above the very bottom exit of a distillation column, for example, wherein the very bottom fraction produced by the column is a salt, an unusable tar, a solid waste product, or a de-minimis stream as would be readily understood by one of reasonable skill in the art.

For purposes herein, distillation columns comprise a distillation zone and a bottom sump zone. The distillation zone includes everything above the bottom sump zone, i.e., between the bottom sump zone and the top of the column. For purposes herein, the bottom sump zone refers to the lower portion of the distillation column in which a liquid reservoir of the higher boiling components is present (e.g., the bottom of a distillation column) from which the bottom or residuum stream flows upon exiting the column. The bottom sump zone may include reboilers, control equipment, and the like.

It is to be understood that the term "passages", "flow paths", "flow conduits", and the like in relation to internal components of a distillation column are used interchangeably to refer to holes, tubes, channels, slits, drains, and the like, which are disposed through and/or which provide a path for liquid and/or vapor to move from one side of the internal component to the other side of the internal component. Examples of passages disposed through a structure such as a liquid distributor of a distillation column include drain holes, drain tubes, drain slits, and the like, which allow a liquid to flow through the structure from one side to another.

Average residence time is defined as the sum total of all liquid volume hold-up for a given phase within a distillation zone divided by the average flow rate of that phase through the distillation zone. The hold-up volume for a given phase can include liquid volume contained in the various internal components of the column including collectors, distributors and the like, as well as liquid contained on trays, within downcomers, and/or within structured or random packed bed sections.

Introducing Lithium Compound

The present invention relates generally to introducing a lithium compound into the reactor to maintain low levels of hydrogen iodide in the reaction medium. Advantageously, lower amounts of hydrogen iodide reduce the amount of hydrogen iodide throughout the system including the gaseous stream from the reactor. Also, the introduction of the lithium compound helps to stabilize the rhodium catalyst, and thus less methyl iodide in the reaction medium may be used in the process to achieve suitable activity. Without introducing the lithium compound, additional rhodium would be needed when the methyl iodide concentration in the reaction medium is decreased. Thus, in one embodiment, there is provided a process for producing acetic acid comprising carbonylating a reactant feed stream comprising methanol, methyl acetate, dimethyl ether, or mixtures thereof in a reactor in the presence of water, rhodium catalyst, iodide salt, and methyl iodide to form a reaction medium; introducing a lithium compound into the reactor; and maintaining a concentration of lithium acetate in the reaction medium from 0.3 to 0.7 wt. %, and the concentration of hydrogen iodide in the reaction medium 0.1 to 1.3 wt. %, wherein the concentration of the rhodium catalyst in the reaction medium is maintained from 300 to 3000 wppm, as rhodium, the concentration of water in the reaction medium is maintained from 0.1 to 4.1 wt. %, and the concentration of methyl acetate in the reaction medium is maintained from 0.6 to 4.1 wt. %. The following amounts are based on the total weight of the reaction medium of the primary carbonylation reactor.

The lithium compound introduced into the reactor is selected from the group consisting of lithium acetate, lithium carboxylates, lithium carbonates, lithium hydroxide, other organic lithium salts, and mixtures thereof. In one embodiment, the lithium compound is soluble in the reaction mixture. In one embodiment, lithium acetate dihydrate may be used as the source of the lithium compound. The type of lithium compound can vary so long as the lithium acetate concentration in the reaction medium is maintained in an amount from 0.3 to 0.7 wt. %.

Lithium acetate reacts with hydrogen iodide by the following equilibrium reaction to form lithium iodide and acetic acid:

LiOAc+HI⇌LiI+HOAc  (I)

Lithium acetate is thought to provide improved control of hydrogen iodide concentration relative to other acetates, such as methyl acetate, present in the reaction medium. Without being bound by theory, lithium acetate is a conjugate base of acetic acid and thus reactive toward hydrogen iodide via an acid-base reaction. This property is thought to result in an equilibrium of the reaction (I) which favors reaction products over and above that produced by the corresponding equilibrium of methyl acetate and hydrogen iodide. This improved equilibrium is favored by water concentrations of less than or equal to 4.1 wt. % in the reaction medium. In addition, the relatively low volatility of lithium acetate compared to methyl acetate allows the lithium acetate to remain in the reaction medium except for volatility losses and small amounts of entrainment into the vapor crude product. In contrast, the relatively high volatility of methyl acetate allows the material to distill into the purification train, rendering methyl acetate more difficult to control. Lithium acetate is much easier to maintain and control in the process at consistent low concentrations of hydrogen iodide. Accordingly, a relatively small amount of lithium acetate may be employed relative to the amount of methyl acetate needed to control hydrogen iodide concentrations in the reaction medium. It has further been discovered that lithium acetate is at least three times more effective than methyl acetate in promoting methyl iodide oxidative addition to the rhodium [I] complex.

In addition, without being bound by theory, lithium acetate is at least three times more effective than methyl acetate in promoting methyl iodide oxidative addition to the rhodium [I] complex.

Advantageously, maintaining a certain concentration of lithium acetate helps to maintain lower concentrations of hydrogen iodide which also lowers the undesirable water gas shift reaction. Thus, by maintaining a lithium acetate concentration from 0.3 to 0.7 wt. % provides considerable benefits to reducing the water gas shift reaction. In addition to suppressing the water gas shift reaction, the addition of the lithium compound, along with the accompanying control of the amount of hydrogen iodide, helps to reduce the corrosion in the reactor and flash vessel.

In addition to suppressing the water gas shift reaction, maintaining concentration of lithium acetate, along with the accompanying control of the amount of hydrogen iodide, helps to reduce the corrosion in the reactor and flash vessel.

The components of the reaction medium are preferably maintained within defined limits to ensure sufficient production of acetic acid. The carbonylation reaction under such conditions advantageously achieves a promotion of the reaction while reducing corrosion effects from hydrogen iodide.

In embodiments, the concentration of lithium acetate in the reaction medium is maintained at greater than or equal to 0.3 wt. %, or greater than or equal to 0.35 wt. %, or greater than or equal to 0.4 wt. %, or greater than or equal to 0.45 wt. %, or greater than or equal to 0.5 wt. %, and/or in embodiments, the concentration of lithium acetate in the reaction medium is maintained at less than or equal to 0.7 wt. %, or less than or equal to 0.65 wt. %, or less than or equal to 0.6 wt. %, or less than or equal to 0.55 wt. %. In one embodiment, the concentration of lithium acetate in the reaction medium is maintained to be from 0.3 to 0.7 wt. %, e.g., from 0.3 to 0.6 wt. %, from 0.35 to 0.6 wt. %, from 0.35 to 0.55 wt. %, or from 0.35 to 0.45 wt. %. Too much lithium acetate in the reaction medium, e.g., greater than 0.7 wt. %. can adversely affect the other compounds in the reaction medium leading to decrease productivity. Also, because lithium acetate as a solid has a significant vapor pressure, lithium acetate may be volatile in a flash vessel, and increasing the lithium acetate in the reaction medium above 0.7 wt. % may further cause lithium to build up in the purification system. Conversely, it has been found that when lithium acetate concentrations falls below 0.3 wt. %, hydrogen iodide concentrations are not sufficiently controlled.

To maintain lithium acetate in such concentrations, a lithium compound may be added. The lithium compound may be introduced continuously, intermittently or during start up. Preferably, lithium compound is introduced intermittently to replace entrainment losses. As stated above, the entrainment losses are low due to the low volatility, so the introduction of lithium salt may be on a long cycle.

In other locations in the acetic acid production system, namely the distillation columns, hydrogen iodide may be controlled by other compounds such as methanol and/or potassium hydroxide. However, these controls for hydrogen iodide are not available in reactor because methanol that is introduced to the reactor is rapidly converted to methyl acetate and to acetic acid. Beneficially, as a result of the control of the lithium acetate concentration, the hydrogen iodide in the reaction medium may be controlled in an amount from 0.1 to 1.3 wt. %, e.g., from 0.1 to 1 wt. %, or from 0.2 to 0.8 wt. %. Hydrogen iodide is known to be more volatile when the concentration of water is less than or equal to 4.1 wt. %, and in operating a reaction under low water conditions, e.g., a water concentration from 0.1 to 4.1 wt. %, the volatile hydrogen iodide may be present in the gaseous streams venting from the reactor. The present invention advantageously reduces hydrogen iodide and thus results in less hydrogen iodide being withdrawn to the flash vessel as well as less hydrogen in the gaseous stream. Although the gaseous stream from the reactor is treated to recover organics and iodide components, an increased amount of hydrogen iodide in the gaseous streams increases the demand the treatment system. Typically, the treatment system is a scrubber, stripper or absorber, such as a pressure-swing absorber. In one embodiment, the gaseous stream comprises hydrogen iodide in an amount of less than or equal to 1 wt. %, e.g., less than or equal to 0.9 wt. %, less than or equal to 0.8 wt. %, less than or equal to 0.7 wt. %, less than or equal to 0.6 wt. %, less than or equal to 0.5 wt. %, and/or the gaseous stream comprises hydrogen iodide in an amount of greater than or equal to 0.001 wt. %, e.g., greater than or equal to 0.005 wt. %, greater than or equal to 0.01 wt. %, greater than or equal to 0.05 wt. %, greater than or equal to 0.1 wt. %. It is also useful to reduce hydrogen iodide by introducing the lithium compound because the treated gaseous stream is returned to the reactor and not purged by the treatment system. Thus, in one embodiment, there is provided carbonylating a reactant feed stream comprising methanol, methyl acetate, dimethyl ether, or mixtures thereof in a reactor in the presence of water, rhodium catalyst, iodide salt and methyl iodide to form a reaction medium, wherein the concentration of water in the reaction medium is maintained from 0.1 to 4.1 wt. %; introducing a lithium compound into the reactor; maintaining a concentration of lithium acetate in the reaction medium from 0.3 to 0.7 wt. %; venting a gaseous stream from the reactor, wherein the gaseous stream comprises hydrogen iodide in an amount of less than or equal to 1 wt. %; and recovering acetic acid from the reaction medium.

Others have determined hydrogen iodide content indirectly by calculation. U.S. Pub. No. 2013/0310603, for example, indicates that iodide ion concentration may be calculated by subtracting the iodide ion concentration derived from the iodide salt form (including iodides derived from co-catalysts and metal iodide) from the total concentration of iodide ion (I⁻). Such indirect calculation techniques are typically inaccurate, resulting in a poor indication of actual hydrogen iodide concentration owing largely to the inaccuracies of the underlying ion measurement methods. In addition, this indirect calculation technique fails to account for other iodide forms because metal cations are measured and incorrectly assumed to be completely associated only with iodide anions while, in fact, the metal cations may be associated with other anions, such as acetate and catalyst anions. In contrast, the direct measurement of hydrogen iodide concentration as described herein advantageously reflects the actual hydrogen iodide concentration in the system, and can result in accuracy as low as 0.01%.

The use of this direct measurement provides for a more accurate measurement of the hydrogen iodide. As such, the lithium acetate concentration can be more effectively maintained and/or controlled. For example, when the hydrogen iodide concentration exceeds a determined threshold, for example, a concentration of 1.3 wt. %, lithium acetate concentration may be increased in the reactor by one of the aforesaid methods described herein. In some embodiments, the portion withdrawn from the reactor may be measured to determine hydrogen iodide concentration in the reaction medium. Thus, in one embodiment, there is provided a process for producing acetic acid comprising carbonylating a reactant feed stream comprising methanol, methyl acetate, dimethyl ether, or mixtures thereof in a reactor in the presence of water, rhodium catalyst, iodide salt and methyl iodide to form a reaction medium, withdrawing a portion of the reaction medium from the reactor, measuring the hydrogen iodide concentration of the withdrawn portion of the reaction medium, introducing a lithium compound into the reactor in response to the measured hydrogen iodide concentration, separating the withdrawn portion of the reaction medium in a flash vessel to form a liquid recycle and a vapor product stream, recovering acetic acid from the reaction medium.

Reaction Medium

According to the present invention, the components of the reaction medium may also be maintained within certain concentration to achieve commercially feasible production rates when the lithium acetate concentration in the reaction medium is maintained from 0.3 to 0.7 wt. %, e.g., from 0.3 to 0.6 wt. %, from 0.35 to 0.6 wt. %, from 0.35 to 0.55 wt. %, or from 0.35 to 0.45 wt. %.

In one embodiment, the carbonylation reaction is conducted in hydrous conditions so as to avoid anhydrous conditions. More preferably, the carbonylation reaction is conducted under low water conditions. As described in U.S. Pat. No. 5,001,259, the entirety of which is incorporated by reference, a reduction in water reduces the energy required to recover acetic acid from the reaction medium. In one embodiment, the concentration of water in the reaction medium is maintained in an amount from 0.1 to 4.1 wt. %, e.g., from 0.1 to 3.1 wt. % or from 0.5 to 2.8 wt. %. Water concentrations above 4.1 wt. %, in particular in the reaction medium, tend to dissociate hydrogen iodide into ions having low volatility. In contrast, when water concentration is less than or equal to 4.1 wt. %, hydrogen iodide remains predominately a molecular gas having a relatively high volatility. Thus controlling hydrogen iodide concentration under low water conditions, e.g., from 0.1 to 4.1 wt. %, provides a direct benefit to preventing hydrogen iodide from passing into the purification train and subsequent problems associated with corrosion. Advantageously, the present invention achieves low hydrogen iodide by maintaining lithium acetate concentrations in the reaction medium from 0.3 to 0.7 wt. %, e.g., from 0.3 to 0.6 wt. %, from 0.35 to 0.6 wt. %, from 0.35 to 0.55 wt. %, or from 0.35 to 0.45 wt. %.

In one embodiment, the reaction medium contains a concentration of the rhodium catalyst in an amount from 300 to 3000 wppm, e.g., from 400 to 3000 wppm, or from 500 to 1500 wppm. In general, the amount of rhodium catalyst in the reaction medium should be stable over its lifetime to avoid loss of rhodium catalyst to precipitation or entrainment into the acetic acid product. This avoids adding excess rhodium catalyst. Also, to avoid excess cost due to the price of the rhodium, it is more efficient to operate the reaction at rhodium concentrations of less than or equal to 1500 wppm, e.g., less than or equal to 1250 wppm, less than or equal to 1000 wppm, less than or equal to 900 wppm.

In one embodiment, the concentration of methyl iodide in the reaction medium is maintained to be from 4 to 13.9 wt. %, e.g., from 4 to 13 wt. %, from 4.1 to 12 wt. %, from 4.1 to 11 wt. %, or from 4.2 to 10 wt. %. Because methyl iodide and lithium acetate exists in equilibrium with methyl acetate and lithium iodide, it is desirable to maintain a concentration of lithium acetate from 0.3 wt. % to 0.7 wt. % in order to maintain the concentration of methyl iodide within the preferred operating concentrations. In addition, the use of lithium acetate in an amount of greater than or equal to 0.3 wt. % may advantageously lower the amount of methyl iodide in the reaction medium. Thus, less methyl iodide needs to be recovered from the vapor on the flash vessel which can lead to debottlenecking the distillation columns. In one embodiment, the vapor on the flash vessel comprises methyl iodide in an amount from 24 to less than or equal to 36 wt. %.

In one embodiment, the concentration of methyl acetate in the reaction medium is maintained from 0.6 to 4.1 wt. %, e.g., from 1.8 to 3.9 wt. %, or from 2 to 3.5 wt. %. Because methyl iodide and lithium acetate exists in equilibrium with methyl acetate and lithium iodide, it is desirable to maintain a concentration of lithium acetate from 0.3 wt. % to 0.7 wt. % in order to maintain the concentration of methyl acetate within the preferred operating concentrations.

The concentration of iodide salt, e.g., lithium iodide, in the reaction medium is not particularly limited, but generally higher amounts of iodide salt are present than methyl acetate and methyl iodide. For purposes of the present invention, iodide salt, and thus iodide salt concentrations, does not include hydrogen iodide. In one embodiment, iodide salt, e.g., lithium iodide may be maintained in amounts from 2 to 20 wt. %, e.g., from 8 to 14 wt. %. In comparison to the relatively low loadings of lithium acetate, the weight ratio of iodide salt to lithium acetate is greater than or equal to 5:1, e.g., greater than or equal to 10:1, from 5:1 to 25:1, from 10:1 to 25:1.

In addition, to the rhodium catalyst and promoters, the reaction medium also comprises acetic acid, which may function as a solvent. The concentration of acetic acid in the reaction medium is generally in amounts of greater than or equal to 30 wt. %, e.g., greater than or equal to 40 wt. % or greater than or equal to 50 wt. %.

Methanol concentrations in the reaction medium are generally low because methanol is readily converted to methyl iodide and methyl acetate under continuous reaction conditions. Thus, adding methanol is unlikely to provide a suitable control for hydrogen iodide concentrations in the reaction medium. In one embodiment, methanol concentration in the reaction medium may be less than or equal to 1 wt. %, e.g., less than or equal to 0.5 wt. % or less than or equal to 0.2 wt. %.

Reaction Step

Exemplary reaction and acetic acid recovery system 100 is shown in FIG. 1. As shown, methanol-containing feed stream 101 and carbon monoxide-containing feed stream 102 are directed to liquid phase carbonylation reactor 105, in which the carbonylation reaction occurs to form acetic acid.

Methanol-containing feed stream 101 may comprise at least one member selected from the group consisting of methanol, dimethyl ether, and methyl acetate. Methanol-containing feed stream 101 may be derived in part from a fresh feed or may be recycled from the system. At least some of the methanol and/or reactive derivative thereof will be converted to, and hence present as, methyl acetate in the liquid medium by esterification with acetic acid.

Typical reaction temperatures for carbonylation may be from 150 to 250° C., with the temperature range of 180 to 225° C. being a preferred range. The carbon monoxide partial pressure in the reactor may vary widely but is typically from 2 to 30 atm, e.g., from 3 to 10 atm. To maintain catalyst activity, the hydrogen partial pressure in the reactor may be from 0.05 to 2 atm, e.g., from 1 to 1.9 atm. However, these higher hydrogen partial pressures tend to increase impurity/byproduct formation. In some embodiments, the present invention may be operated with a lower hydrogen partial pressure of less than or equal to 0.05 atm, e.g., less than or equal to 0.04 atm, less than or equal to 0.03 atm, or less than or equal to 0.02 atm. Lower hydrogen partial pressure may be used to reduce impurity/byproduct formation, but is avoided due to the impact on catalyst activity. Advantageously, the present invention may be operated at a lower hydrogen partial pressure because the concentration of lithium acetate in the reaction medium is maintained from 0.3 to 0.7 wt. %. In one embodiment, there is provided a process for carbonylating a reactant feed stream comprising methanol, methyl acetate, dimethyl ether, or mixtures thereof in a reactor in the presence of water, rhodium catalyst, iodide salt and methyl iodide to form a reaction medium, wherein the reactor has a hydrogen partial pressure of less than or equal to 0.05 atm, introducing a lithium compound into the reactor, and maintaining a concentration of lithium acetate in the reaction medium from 0.3 to 0.7 wt. %, wherein the concentration of the rhodium catalyst in the reaction medium is maintained from 300 to 3000 wppm, as rhodium, the concentration of water in the reaction medium is maintained from 0.1 to 4.1 wt. %, and the concentration of methyl acetate in the reaction medium is maintained from 0.6 to 4.1 wt. %.

Because of the partial pressure of by-products and the vapor pressure of the contained liquids, the total reactor pressure may range from 15 to 40 atm. The production rate of acetic acid may be from 5 to 50 mol/L·h, e.g., from 10 to 40 mol/L·h, and preferably from 15 to 35 mol/L·h. High catalyst activity, as determined by the production rate, may be achieved by maintaining a concentration of lithium acetate in the reaction medium from 0.3 to 0.7 wt. %. In one embodiment, maintaining a concentration of lithium acetate in the reaction medium from 0.3 to 0.7 wt. % is greater than or equal to 10 mol/L·h, e.g., greater than or equal to 15 mol/L·h, or greater than or equal to 20 mol/L·h.

In one embodiment, the production rate of acetic acid is from 10 mol/L·h to 40 mol/L·h and wherein in the reaction medium the concentration of lithium acetate is maintained from 0.3 to 0.6 wt. %, the concentration of the rhodium catalyst is maintained from 800 to 3000 wppm, the concentration of water is maintained from 0.1 to 3.1 wt. %, the concentration of methyl acetate is maintained from 1.8 to 3.9 wt. %, and the concentration of hydrogen iodide is maintained from 0.1 to 1 wt. %.

In one embodiment, the production rate of acetic acid is from 15 mol/L·h to 35 mol/L·h and wherein in the reaction medium the concentration of lithium acetate is maintained from 0.35 to 0.55 wt. %, the concentration of the rhodium catalyst is maintained from 900 to 1500 wppm, the concentration of water is maintained from 0.5 to 2.8 wt. %, the concentration of methyl acetate is maintained from 2 to 3.5 wt. %, and the concentration of hydrogen iodide is maintained from 0.2 to 0.8 wt. % in the reaction medium.

Carbonylation reactor 105 is preferably either a mechanically stirred vessel, a vessel with an educted or pump-around mixing, or bubble-column type vessel, with or without an agitator, within which the reacting liquid or slurry contents are maintained, preferably automatically, a predetermined level, which preferably remains substantially constant during normal operation. Into carbonylation reactor 105, fresh methanol, carbon monoxide, and sufficient water are continuously introduced as needed to maintain suitable concentrations in the reaction medium.

For the purposes of the present invention, the metal catalyst is a rhodium catalyst. The rhodium catalyst may be added in any suitable form such that rhodium is in the catalyst solution as an equilibrium mixture including $[Rh(CO)_2I_2]$-anion, as is well known in the art. Iodide salts optionally maintained in the reaction mixtures of the processes described herein may be in the form of a soluble salt of an alkali metal or alkaline earth metal, quaternary ammonium, phosphonium salt or mixtures thereof. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; 5,144,068 and 7,005,541, which are incorporated herein by reference in their entirety.

The halogen-containing catalyst promoter of the catalyst system consists of a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter may include methyl halide, and more preferably methyl iodide.

In some embodiments, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously.

The carbonylation reaction of methanol to acetic acid product may be carried out by contacting the methanol feed with gaseous carbon monoxide bubbled through an acetic acid solvent reaction medium containing the rhodium catalyst, methyl iodide promoter, methyl acetate, and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable.

In one exemplary embodiment, in reaction medium the concentration of lithium acetate is maintained from 0.3 to 0.6 wt. %, the concentration of the rhodium catalyst is maintained from 800 to 3000 wppm, the concentration of water is maintained from 0.1 to 3.1 wt. %, the concentration of methyl acetate is maintained from 1.8 to 3.9 wt. %, and the concentration of hydrogen iodide is maintained from 0.1 to 1 wt. %. The reaction medium may further comprise methyl iodide in an amount from 4 to 13.9 wt. % and iodide salt in an amount from 2 to 20 wt. %.

In another exemplary embodiment, in the reaction medium the concentration of lithium acetate is maintained from 0.35 to 0.55 wt. %, the concentration of the rhodium catalyst is maintained from 900 to 1500 wppm, the concentration of water is maintained from 0.5 to 2.8 wt. %, the concentration of methyl acetate is maintained from 2 to 3.5 wt. %, and the concentration of hydrogen iodide is maintained from 0.2 to 0.8 wt. % in the reaction medium. The reaction medium may further comprise methyl iodide in an amount from 4 to 13.9 wt. % and iodide salt in an amount from 2 to 20 wt. %.

The reaction medium may also contain impurities that should be controlled to avoid byproduct formation. One impurity in the reaction medium may be ethyl iodide, which is difficult to separate from acetic acid. Applicant has further discovered that the formation of ethyl iodide may be affected by numerous variables, including the concentration of acetaldehyde, ethyl acetate, methyl acetate and methyl iodide in the reaction medium. Additionally, ethanol content in the methanol source, hydrogen partial pressure and hydrogen content in the carbon monoxide source have been discovered to affect ethyl iodide concentration in the reaction medium and, consequently, propionic acid concentration in the final acetic acid product.

In embodiments, the propionic acid concentration in the acetic acid product may further be maintained below 250 wppm by maintaining the ethyl iodide concentration in the reaction medium at less than or equal to 750 wppm without removing propionic acid from the acetic acid product.

In embodiments, the ethyl iodide concentration in the reaction medium and propionic acid in the acetic acid product may be present in a weight ratio from 3:1 to 1:2. In embodiments, the acetaldehyde:ethyl iodide concentration in the reaction medium is maintained at a weight ratio from 2:1 to 20:1.

In embodiments, the ethyl iodide concentration in the reaction medium may be maintained by controlling at least one of the hydrogen partial pressure, the methyl acetate concentration, the methyl iodide concentration, and/or the acetaldehyde concentration in the reaction medium.

In embodiments, the concentration of ethyl iodide in the reaction medium is maintained/controlled to be less than or equal to 750 wppm, or e.g., less than or equal to 650 wppm, or less than or equal to 550 wppm, or less than or equal to 450 wppm, or less than or equal to 350 wppm. In embodiments, the concentration of ethyl iodide in the reaction medium is maintained/controlled at greater than or equal to 1 wppm, or e.g., 5 wppm, or 10 wppm, or 20 wppm, or 25 wppm, and less than or equal to 650 wppm, or e.g., 550 wppm, or 450 wppm, or 350 wppm.

In embodiments, the weight ratio of ethyl iodide in the reaction medium to propionic acid in the acetic acid product may range from 3:1 to 1:2, or e.g., from 5:2 to 1:2, or from 2:1 to 1:2, or from 3:2 to 1:2.

In embodiments, the weight ratio of acetaldehyde to ethyl iodide in the reaction medium may range from 20:1 to 2:1, or e.g., from 15:1 to 2:1 or from 9:1 to 2:1.

In a typical carbonylation process, carbon monoxide is continuously introduced into the carbonylation reactor, desirably below the agitator, which may be used to stir the contents. The gaseous feed preferably is thoroughly dispersed through the reacting liquid by this stirring means. Gaseous purge stream 106 desirably is vented from the reactor 105 to prevent buildup of gaseous by-products and to maintain a set carbon monoxide partial pressure at a given total reactor pressure. In one embodiment, the gaseous purge stream 106 contains low amounts of hydrogen iodide of less than or equal to 1 wt. %, e.g., less than or equal to 0.9 wt. %, less than or equal to 0.8 wt. %, less than or equal to 0.7 wt. %, less than or equal to 0.6 wt. %, less than or equal to 0.5 wt. % and/or the gaseous stream comprises hydrogen iodide in an amount of greater than or equal to 0.001 wt. %, e.g., greater than or equal to 0.005 wt. %, greater than or equal to 0.01 wt. %, greater than or equal to 0.05 wt. %, greater than or equal to 0.1 wt. %. As stated above, hydrogen iodide in excess of these amounts may increase the duty on the treatment system, e.g., stripper, scrubber, or absorber, to prevent hydrogen iodide from being purged. The temperature of the reactor may be controlled and the carbon monoxide feed is introduced at a rate sufficient to maintain the desired total reactor pressure. Stream 113 comprising the liquid reaction medium exits reactor 105.

The acetic acid production system preferably includes separation system 108 employed to recover the acetic acid and recycle rhodium catalyst, methyl iodide, methyl acetate, and other system components within the process. One or more of the recycle streams may be combined prior to being introduced into the reactor. The separation system also preferably controls water and acetic acid content in the carbonylation reactor. In one embodiment, the separation system may also remove permanganate reducing compound ("PRC"). PRC's may include acetaldehyde, acetone, methyl ethyl ketone, butylaldehyde, crotonaldehyde, 2-ethyl crotonaldehyde, 2-ethyl butyraldehyde, and the aldol condensation products thereof. In one embodiment, a suitable potassium permanganate test is JIS K1351 (2007).

The reaction medium is drawn off from the carbonylation reactor 105 at a rate sufficient to maintain a constant level therein and is provided to flash vessel 110 via stream 113. The flash separation may be carried out at a temperature from 80° C. to 200° C., under an absolute pressure from 1 to 10 atm. The reaction medium is separated in a flash separation step to obtain a vapor product stream 112 comprising acetic acid and liquid recycle stream 111 comprising a catalyst-containing solution. Lithium acetate remains in the catalyst-containing solution and is preferably not volatilized in flash vessel. There are small amounts of entrained lithium acetate that require periodic, intermittent replacements. The catalyst-containing solution may be predominantly acetic acid containing the rhodium and the iodide salt along with lesser quantities of methyl acetate, methyl iodide, lithium acetate and water and is recycled to the reactor, as discussed above. Prior to returning liquid recycle to the reactor, a slip stream may pass through a corrosion metal removal bed, such as an ion exchange bed, to remove any entrained corrosion metals, such as nickel, iron, chromium, and molybdenum, as described in U.S. Pat. No. 5,731,252, which is incorporated herein by reference in its entirety. Also, the corrosion metal removal bed may be used to remove nitrogen compounds, such as amines, as described in U.S. Pat. No. 8,697,908, which is incorporated herein by reference in its entirety.

In addition to acetic acid, vapor product stream 112 also comprises methyl iodide, methyl acetate, water, PRC's and other iodide compounds. Dissolved gases exiting reactor 105 and entering flash vessel 110 comprise a portion of the carbon monoxide and may also contain gaseous by-products such as methane, hydrogen, and carbon dioxide. Such dissolved gases exit flash vessel 110 as part of the vapor product stream 112. In one embodiment, carbon monoxide in gaseous purge stream 106 may be fed to the base of flash vessel 110 to enhance rhodium stability.

In one embodiment, vapor product stream 112 comprises acetic acid, methyl iodide, methyl acetate, water, acetaldehyde, and hydrogen iodide. In one embodiment, vapor product stream 112 comprises acetic acid in an amount from 45 to 75 wt. %, methyl iodide in an amount from 20 to 50 wt. %, methyl acetate in an amount of less than or equal to 9 wt. %, and water in an amount of less than or equal to 15 wt. %, based on the total weight of the vapor product stream. In another embodiment, vapor product stream 112 comprises acetic acid in an amount from 45 to 75 wt. %, methyl iodide in an amount from 24 to less than or equal to 36 wt. %, methyl acetate in an amount of less than or equal to 9 wt. %, and water in an amount of less than or equal to 15 wt. %, based on the total weight of the vapor product stream. More preferably, vapor product stream 112 comprises acetic acid in an amount from 55 to 75 wt. %, methyl iodide in an amount from 24 to 35 wt. %, methyl acetate in an amount from 0.5 to 8 wt. %, and water in an amount from 0.5 to 14 wt. %. In yet a further preferred embodiment, vapor product stream 112 comprises acetic acid in an amount from 60 to 70 wt. %, methyl iodide in an amount from 25 to 35 wt. %, methyl acetate in an amount from 0.5 to 6.5 wt. %, and water in an amount from 1 to 8 wt. %. The acetaldehyde concentration in the vapor product stream may be in an amount from 0.005 to 1 wt. %, based on the total weight of the vapor product stream, e.g., from 0.01 to 0.8 wt. %, or from 0.01 to 0.7 wt. %. In some embodiments, the acetaldehyde may be present in amounts less than or equal to 0.01 wt. %. Vapor product stream 112 may comprise hydrogen iodide in an amount less than or equal to 1 wt. %, based on the total weight of the vapor product stream, e.g., less than or equal to 0.5 wt. %, or less than or equal to 0.1 wt. %. Vapor product stream 112 is preferably substantially free of, i.e., contains less than or equal to 0.0001 wt. %, propionic acid, based on the total weight of the vapor product stream.

Liquid recycle stream 111 comprises acetic acid, the metal catalyst, corrosion metals, as well as other various compounds. In one embodiment, liquid recycle stream comprises acetic acid in an amount from 60 to 90 wt. %, metal catalyst in an amount from 0.01 to 0.5 wt. %, corrosion metals (e.g., nickel, iron and chromium) in a total amount from 10 to 2500 wppm, lithium iodide in an amount from 5 to 20 wt. %, methyl iodide in an amount from 0.5 to 5 wt. %, methyl acetate in an amount from 0.1 to 5 wt. %, water in an amount from 0.1 to 8 wt. %, acetaldehyde in an amount of less than or equal to 1 wt. % (e.g., from 0.0001 to 1 wt. % acetaldehyde), and hydrogen iodide in an amount of less than or equal to 0.5 wt. % (e.g., from 0.0001 to 0.5 wt. % hydrogen iodide).

Recovery of Acetic Acid

The distillation and recovery of acetic acid is not particularly limited for the purposes of the present invention.

First Column

As shown in FIG. 1, vapor product stream 112 is directed to a first column 120, also referred to as a light ends column. Distillation yields a low-boiling overhead vapor stream 122, a purified acetic acid product that preferably is removed via a side stream 124, and a high boiling residue stream 121. In one embodiment, low-boiling overhead vapor stream 122 comprises water, methyl acetate, methyl iodide, and carbonyl impurities. The amount of water in low-boiling overhead vapor stream 122 is generally greater than or equal to 5 wt. %. Side stream 124 may comprise acetic acid in an amount from 90 to 98 wt. %, water in an amount from 1 to 2.5 wt. %, methyl iodide in an amount from 0.1 to 5 wt. %, and methyl acetate in an amount from 0.1 to 5 wt. %. Acetic acid removed via side stream 124 is preferably subjected to further purification, such as in a second column 125, also referred to as a drying column. Second column 125 separates side stream 124 to form overhead stream 126 comprised primarily of water and bottoms stream 127 comprised primarily of acetic acid. Overhead stream 126 may comprise water in an amount from 50 to 75 wt. %. Methyl acetate and methyl iodide are also removed from the side stream and concentrated in overhead stream 126.

Decanter

Low-boiling overhead vapor stream 122 separated from first column 120 contains a reaction component, such as methyl iodide, methyl acetate, and water, and it is preferable to retain these reaction components within the process. Low-boiling overhead vapor stream 122 is condensed by a heat exchanger into stream 133, which may be recycled to reactor 105 and/or refluxed first column 120. An offgas component may be vented via line 132 from condensed low-boiling overhead vapor stream 124.

In some embodiments, low-boiling overhead vapor stream 122 preferably may be condensed and directed to an overhead phase separation unit, such as overhead decanter (not shown). Conditions are desirably maintained such that the condensed low-boiling overhead vapor stream 122, once in decanter, may separate to form a light liquid phase, enriched in water, and a heavy liquid phase, enriched in methyl iodide. The phase separation should maintain two separate phases, without forming a third phase or emulsion between the phases. An offgas component may be vented from decanter. In embodiments, the average residence time of the condensed low-boiling overhead vapor stream 122 in overhead decanter is greater than or equal to 1 minute, e.g., greater than or equal to 3 minutes, greater than or equal to 5 minutes, greater than or equal to 10 minutes, and/or the average residence time is less than or equal to 60 minutes, e.g., less than or equal to 45 minutes, or less than or equal to 30 minutes, or less than or equal to 25 minutes. In addition, overhead decanter may be arranged and constructed to maintain a low interface level to prevent an excess hold up of methyl iodide.

Second Column

Drying column bottoms stream 127 preferably comprises or consists essentially of acetic acid. In preferred embodiments, drying column bottoms stream 127 comprises acetic acid in an amount greater than or equal to 90 wt. %, e.g., greater than or equal to 95 wt. % or greater than or equal to 98 wt. %. Drying column bottoms stream 127 may be further processed, e.g., by passing through an ion exchange resin, prior to being stored or transported for commercial use.

Similarly, overhead stream 126 from second column 125 contains a reaction component, such as methyl iodide, methyl acetate, and water, and it is preferable to retain these reaction components within the process. Overhead stream 126 is condensed by a heat exchanger into stream 136, which is recycled to reactor 105 and/or refluxed second column 125. An offgas component may be vented via line 135 from condensed low-boiling overhead vapor stream 126. Similar to the condensed low-boiling overhead vapor stream in stream 133, condensed overhead stream in stream 136 may also be separated to form an aqueous phase and an organic phase, and these phases may be recycled or refluxed as needed to maintain the concentrations in the reaction medium.

PRC Removal System

Although not shown, a portion of condensed low-boiling overhead vapor stream 122, such as either light liquid phase and/or heavy liquid phase may be separated and directed to acetaldehyde or PRC removal system to recover methyl iodide and methyl acetate during the acetaldehyde removal process. Light liquid phase and/or heavy liquid phase each contain PRC's and the process may include removing carbonyl impurities, such as acetaldehyde, that deteriorate the quality of the acetic acid product and may be removed in suitable impurity removal columns and absorbers as described in U.S. Pat. Nos. 6,143,930; 6,339,171; 7,223,883; 7,223,886; 7,855,306; 7,884,237; 8,889,904; and US Pub. Nos. 2006/0011462, which are incorporated herein by reference in their entirety. Carbonyl impurities, such as acetaldehyde, may react with iodide catalyst promoters to form alkyl iodides, e.g., ethyl iodide, propyl iodide, butyl iodide, pentyl iodide, hexyl iodide, etc. Also, because many impurities originate with acetaldehyde, it is desirable to remove carbonyl impurities from the liquid light phase.

The portion of light liquid phase and/or heavy liquid phase fed to the acetaldehyde or PRC removal system may vary from 1% to 99% of the mass flow of either the light liquid phase and/or heavy liquid phase, e.g., from 1 to 50%, from 2 to 45%, from 5 to 40%, 5 to 30% or 5 to 20%. Also, in some embodiments, a portion of both the light liquid phase and heavy liquid phase may be fed to the acetaldehyde or PRC removal system. The portion of the light liquid phase not fed to the acetaldehyde or PRC removal system may be refluxed to the first column or recycled to the reactor, as described herein. The portion of the heavy liquid phase not fed to the acetaldehyde or PRC removal system may be recycled to the reactor. Although a portion of heavy liquid phase may be refluxed to the first column, it is more desirable to return the methyl iodide enriched heavy liquid phase to the reactor.

In one embodiment, a portion of light liquid phase and/or heavy liquid phase is fed to a distillation column which enriches the overhead thereof to have acetaldehyde and methyl iodide. Depending on the configuration, there may be two separate distillation columns, and the overhead of the second column may be enriched in acetaldehyde and methyl iodide. Dimethyl ether, which may be formed in-situ, may also be present in the overhead. The overhead may be subject to one or more extraction stages to remove a raffinate enriched in methyl iodide and an extractant. A portion of the raffinate may be returned to the distillation column, first column, overhead decanter and/or reactor. For example, when the heavy liquid phase is treated in the PRC removal system, it may be desirable to return a portion the raffinate to either the distillation column or reactor. Also, for example, when light liquid phase is treated in the PRC removal system, it may be desirable to return a portion the raffinate to either the first column, overhead decanter, or reactor. In some embodiments, the extractant may be further distilled to remove water, which is returned to the one or more extraction stages. A portion the raffinate, which contains more methyl acetate and methyl iodide than light liquid phase, may also be recycled to reactor and/or refluxed to first column. To recover residue organics and iodides from the vent stream, in particular lines 106, 132, and 135, these lines may be fed to a scrubber that operates with chilled methanol and/or acetic acid to remove methyl acetate and methyl iodide. A suitable scrubber is described in U.S. Pat. No. 8,318,977, which is incorporated herein by reference in its entirety.

The distillation columns of the present invention may be a conventional distillation column, e.g., a plate column, a packed column, and others. Plate columns may include a perforated plate column, bubble-cap column, Kittel tray column, uniflux tray, or a ripple tray column. For a plate column, the theoretical number of plates is not particularly limited and depending on the species of the component to be separated, may include up to 80 plates, e.g., from 2 to 80, from 5 to 60, from 5 to 50, or more preferably from 7 to 35. The distillation column may include a combination of different distillation apparatuses. For example, a combination of bubble-cap column and perforated plate column may be used as well as a combination of perforated plate column and a packed column.

The distillation temperature and pressure in the distillation system can suitably be selected depending on the condition such as the species of the objective carboxylic acid and the species of the distillation column, or the removal target selected from the lower boiling point impurity and the higher boiling point impurity according to the composition of the feed stream. For example, in a case where the purification of acetic acid is carried out by the distillation column, the inner pressure of the distillation column (usually, the pressure of the column top) may be from 0.01 to 1 MPa, e.g., from 0.02 to 0.7 MPa, and more preferably from 0.05 to 0.5 MPa in terms of gauge pressure. Moreover, the distillation temperature for the distillation column, namely the inner temperature of the column at the temperature of the column top, can be controlled by adjusting the inner pressure of the column, and, for example, may be from 20 to 200° C., e.g., from 50 to 180° C., and more preferably from 100 to 160° C.

The material of each member or unit associated with the distillation system, including the columns, valves, condensers, receivers, pumps, reboilers, and internals, and various lines, each communicating to the distillation system may be made of suitable materials such as glass, metal, ceramic, or combinations thereof, and is not particularly limited to a specific one. According to the present invention, the material of the foregoing distillation system and various lines are a transition metal or a transition-metal-based alloy such as iron alloy, e.g., a stainless steel, nickel or nickel alloy, zirconium or zirconium alloy thereof, titanium or titanium alloy thereof, or aluminum alloy. Suitable iron-based alloys include those containing iron as a main component, e.g., a stainless steel that also comprises chromium, nickel, molybdenum and others. Suitable alloys include those containing nickel as a main component and one or more of chromium, iron, cobalt, molybdenum, tungsten, manganese, and others, e.g., HASTELLOY™ and INCONEL™. Corrosion-resistant metals may be particularly suitable as materials for the distillation system and various lines.

Guard Bed

Carboxylic acid streams, e.g., acetic acid streams, that are contaminated with a halides and/or corrosion metals may be contacted with the ion exchange resin composition under a wide range of operating conditions. Preferably, the ion exchange resin composition is provided in a guard bed. The use of guard beds to purify contaminated carboxylic acid streams is well documented in the art, for example, U.S. Pat. Nos. 4,615,806; 5,653,853; 5,731,252; and 6,225,498, which are hereby incorporated by reference in their entireties. Generally, a contaminated liquid carboxylic acid stream is contacted with an ion exchange resin composition, which is preferably disposed in the guard bed. The halide contaminants, e.g., iodide contaminants, react with the metal to form metal iodides. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

In one embodiment, due to the presence of lithium acetate in the reaction medium, there may be some undesirable carryover of lithium. Without being bound by theory lithium derived from the lithium acetate in the reaction may carry over in the acetic acid product. Lithium may cause displacement having metal-exchanged strong acid cation site. By using a cation exchanger to remove lithium prior to the use of a resin having metal-exchanged strong acid cation sites, the displacement of silver, mercury, palladium and/or rhodium from the metal-exchanged sites by the lithium is reduced or eliminated. According to one embodiment, the lithium, and preferably lithium cation, is removed prior to the iodide removal to prevent displacement in the metal ion-exchange resin.

Lithium has also been found to be entrained in the crude acid product in the absence of heavy ends and other finishing apparatus. Even in very small amounts of 10 wppb of lithium in the crude acid product may cause problem for removing iodides. The lithium in the acid-containing crude acid product exiting the drying column of an acetic acid process, e.g., the last column in the primary purification train, may be in an amount up to or equal to 10 wppm of lithium, e.g., up to or equal to 5 wppm, up to or equal to 1 wppm, up to or equal to 500 wppb, up to or equal to 300 wppb, or up to or equal to 100 wppb. In terms of ranges, the crude acid product may comprise lithium in an amount from 0.01 wppm to 10 wppm, e.g., from 0.05 wppm to 5 wppm or from 0.05 wppm to 1 wppm. By utilizing a cationic exchanger in the acid form before introducing the crude acid product to a metal-exchanged resin, significant amounts of lithium can be removed. For example greater than or equal to 90 wt. % of the lithium in the stream might be removed by the cationic exchanger, e.g., 95 wt. % or 99 wt. %. Thus, the stream exiting the acid-form cationic exchanger may contain less than or equal to 50 wppb lithium, e.g., less than or equal to 10 wppb, or less than or equal to 5 wppb. Such removal of the lithium can greatly extend the life of the metal-exchanged resin.

Thus, in one embodiment there is provided a process for producing acetic acid comprising carbonylating at least one member selected from the group consisting of methanol, dimethyl ether, and methyl acetate in the presence of water, a rhodium catalyst, methyl iodide and a lithium iodide, to form a reaction medium in a reactor, wherein the concentration of lithium acetate in the reaction medium is maintained at less than or equal to 0.7 wt. %, separating the reaction medium to form a liquid recycle stream and a vapor product stream, separating the vapor product stream in up to 2 distillation columns in a primary purification train to produce a crude acid product comprising acetic acid and at least one lithium cation, which may be derived from the lithium iodide and/or lithium acetate, contacting the crude acetic acid product with a cationic exchanger in the acid form to produce an intermediate acid product, and contacting the intermediate acetic acid product with a metal-exchanged ion exchange resin having acid cation exchange sites to produce a purified acetic acid.

The pressure during the contacting step is limited only by the physical strength of the resin. In one embodiment, the contacting is conducted at pressures ranging from 0.1 MPa to 1 MPa, e.g., from 0.1 MPa to 0.8 MPa or from 0.1 MPa to 0.5 MPa. For convenience, however, both pressure and temperature preferably may be established so that the contaminated carboxylic acid stream is processed as a liquid. Thus, for example, when operating at atmospheric pressure, which is generally preferred based on economic considerations, the temperature may range from 17° C. (the freezing point of acetic acid) to 118° C. (the boiling point of acetic acid). It is within the purview of those skilled in the art to determine analogous ranges for product streams comprising other carboxylic acid compounds. The temperature of the contacting step preferably is kept relatively low to minimize resin degradation. In one embodiment, the contacting is conducted at a temperature ranging from 25° C. to 120° C., e.g., from 25° C. to 100° C. or from 50° C. to 100° C. Some cationic macroreticular resins typically begin degrading (via the mechanism of acid-catalyzed aromatic desulfonation) at temperatures of 150° C. Carboxylic acids having up to 5 carbon atoms, e.g., up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for halide removal.

The configuration of the guard bed within an acetic acid purification train may vary widely. For example, the guard bed may be configured after a drying column. Additionally or alternatively, the guard be may be configured after a heavy ends removal column or finishing column. Preferably the guard bed is configured in a position wherein the temperature acetic acid product stream is low, e.g., less than or equal to 120° C. or less than or equal to 100° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

In one embodiment, the flow rate through the guard bed ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

To avoid exhausting the resin with a purified acetic acid product that is high in total iodide concentration, in one embodiment the purified acetic acid product in bottoms stream 127 is contacted with a guard bed when total iodide concentration of the purified acetic acid product is less than or equal to 1 wppm. Total iodide concentration includes iodide from both organic sources, $C_1$ to $C_{14}$ alkyl iodides, and inorganic sources, such as hydrogen iodide. A purified acetic acid composition is obtained as a result of the guard bed treatment. The purified acetic acid composition, in one embodiment, comprises less than or equal to 100 wppb iodides, e.g., less than or equal to 90 wppb, less than or equal to 50 wppb, or less than or equal to 25 wppb. In one embodiment, the purified acetic acid composition comprises less than or equal to 1000 wppb corrosion metals, e.g., less than or equal to 750 wppb, less than or equal to 500 wppb, or less than or equal to 250 wppb. For purposes of the present invention, corrosion metals include metals selected from the group consisting of nickel, iron, chromium, molybdenum and combinations thereof. In terms of ranges, the purified acetic acid composition may comprise from 0 to 100 wppb iodides, e.g., from 1 to 50 wppb, and/or from 0 to 1000 wppb corrosion metals, e.g., from 1 to 500 wppb. In other embodiments, the guard bed removes at least 25 wt. % of the iodides from the crude acetic acid product, e.g., at least 50 wt. % or at least 75 wt. %. In one embodiment, the guard bed removes at least 25 wt. % of the corrosion metals from the crude acetic acid product, e.g., at least 50 wt. % or at least 75 wt. %.

As is evident from the figures and text presented above, a variety of embodiments are contemplated.

E1. A process for producing acetic acid comprising:
carbonylating a reactant feed stream comprising methanol, methyl acetate, dimethyl ether, or mixtures thereof in a reactor in the presence of water, rhodium catalyst, iodide salt, and methyl iodide to form a reaction medium;
introducing a lithium compound into the reactor; and
maintaining a concentration of lithium acetate in the reaction medium from 0.3 to 0.7 wt. %, and the concentration of hydrogen iodide in the reaction medium from 0.1 to 1.3 wt. %;
wherein the concentration of the rhodium catalyst in the reaction medium is maintained from 300 to 3000 wppm, as rhodium, the concentration of water in the reaction medium is maintained from 0.1 to 4.1 wt. %, and the concentration of methyl acetate in the reaction medium is maintained from 0.6 to 4.1 wt. %.

E2. The process according to embodiment E1, wherein the lithium compound is selected from the group consisting of lithium acetates, lithium carboxylates, lithium carbonates, lithium hydroxides, and mixtures thereof.

E3. The process according to embodiment E1 to E2, wherein the concentration of methyl iodide in the reaction medium is maintained from 4 to 13.9 wt. %, and preferably from 4 to 13 wt. %.

E4. The process according to any one of embodiments E1 to E3, wherein the concentration of iodide salt in the reaction medium is maintained from 2 to 20 wt. %.

E5. The process according to any one of embodiments E1 to E4, wherein the concentration of iodide salt in the reaction medium is maintained from 8 to 14 wt. %.

E6. The process according to any one of embodiments E1 to E5, wherein is the production rate of acetic acid is from 5 mol/L·h to 50 mol/L·h.

E7. The process according to any one of embodiments E1 to E6, wherein the reaction is conducted while maintaining a carbon monoxide partial pressure from 2 to 30 atm and a hydrogen partial pressure in the reactor that is less than or equal to 0.04 atm.

E8. The process according to any one of embodiments E1 to E7, wherein the concentration of methyl acetate in the reaction medium is greater than or equal to the concentration of the lithium acetate.

E9. The process according to any one of embodiments E1 to E8, wherein the reaction is conducted at a temperature from 150° C. to 250° C. and at a pressure from 15 to 40 atm.

E10. The process according to any one of embodiments E1 to E9, wherein the weight ratio of iodide salt to the lithium compound is greater than or equal to 5:1.

E11. The process according to any one of embodiments E1 to E9, wherein in the reaction medium, the concentration of lithium acetate is maintained from 0.3 to 0.6 wt. %, the concentration of the rhodium catalyst is maintained from 800 to 3000 wppm, the concentration of water is maintained from 0.1 to 3.1 wt. %, the concentration of methyl acetate is maintained from 1.8 to 3.9 wt. %, and the concentration of hydrogen iodide is maintained from 0.1 to 1 wt. %.

E12. The process according to any one of embodiments E1 to E9, wherein in the reaction medium, the concentration of lithium acetate is maintained from 0.35 to 0.55 wt. %, the concentration of the rhodium catalyst is maintained from 900 to 1500 wppm, the concentration of water is maintained from 0.5 to 2.8 wt. %, the concentration of methyl acetate is maintained from 2 to 3.5 wt. %, and the concentration of hydrogen iodide is maintained from 0.2 to 0.8 wt. % in the reaction medium.

E13. The process according to any one of embodiments E1 to E9, wherein the production rate of acetic acid is from 10 mol/L·h to 40 mol/L·h and wherein in the reaction medium, the concentration of lithium acetate is maintained from 0.3 to 0.6 wt. %, the concentration of the rhodium catalyst is maintained from 800 to 3000 wppm, the concentration of water is maintained from 0.1 to 3.1 wt. %, the concentration of methyl acetate is maintained from 1.8 to 3.9 wt. %, and the concentration of hydrogen iodide is maintained from 0.1 to 1 wt. %.

E14. The process according to any one of embodiments E1 to E9, wherein the production rate of acetic acid is from 15 mol/L·h to 35 mol/L·h and wherein in the reaction medium, the concentration of lithium acetate is maintained from 0.35 to 0.55 wt. %, the concentration of the rhodium catalyst is maintained from 900 to 1500 wppm, the concentration of water is maintained from 0.5 to 2.8 wt. %, the concentration of methyl acetate is maintained from 2 to 3.5 wt. %, and the concentration of hydrogen iodide is maintained from 0.2 to 0.8 wt. % in the reaction medium.

E15. The process according to any one of embodiments E1 to E9, wherein the concentration of lithium acetate in the reaction medium is maintained from 0.3 to 0.6 wt. %.

E16. The process according to any one of embodiments E1 to E9, wherein the concentration of hydrogen iodide in the reaction medium is maintained from 0.1 to 1 wt. %, and preferably from 0.2 to 0.8 wt. %.

E17. A process for producing acetic acid comprising:
  carbonylating a reactant feed stream comprising methanol, methyl acetate, dimethyl ether, or mixtures thereof in a reactor in the presence of water, rhodium catalyst, iodide salt, and methyl iodide to form a reaction medium, wherein the concentration of water in the reaction medium is maintained from 0.1 to 4.1 wt. %;
  introducing a lithium compound into the reactor;
  maintaining a concentration of lithium acetate in the reaction medium from 0.3 to 0.7 wt. %;
  venting a gaseous stream from the reactor, wherein the gaseous stream comprises hydrogen iodide in an amount of less than or equal to 1 wt. %, and
  recovering acetic acid from the reaction medium.

E18. The process according to embodiment E17, wherein the gaseous stream comprises hydrogen iodide in an amount from 0.001 to 1 wt. %.

E19. The process according to any one of embodiments E17 to E18, wherein the concentration of the rhodium catalyst in the reaction medium is maintained from 300 to 3000 wppm, as rhodium, the concentration of water in the reaction medium is maintained from 0.1 to 4.1 wt. %, and the concentration of methyl acetate in the reaction medium is maintained from 0.6 to 4.1 wt. %.

E20. The process according to any one of embodiments E17 to E19, further comprising scrubbing the gaseous stream to remove hydrogen iodide from a purge stream.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

EXAMPLES

The present invention will be better understood in view of the following non-limiting example.

To demonstrate the effect of lithium acetate on the promotional effect of lithium acetate the following experiments were conducted to determine the effect of methyl iodide oxidative addition to the rhodium complex, $Li[RhI_2(CO)_2]$. In the carbonylation reaction, this may be the rate limiting step. A number of variables can strongly effect the activity of the catalytic system as a whole. A number of complex interrelationships which are present in the operating catalyst were either absent or considerably simplified in this example. In general, methyl iodide was added to an acetic acid solution containing 1200 ppm Rh in the form of $Li[RhI_2(CO)_2]$, 2% water and the individual promoter in a glovebox under nitrogen atmosphere at 25° C. The solution was transferred to a sample cell and sealed for FTIR measurement in a nitrogen purged sample chamber. The kinetics of the reaction of methyl iodide with $Li[RhI_2(CO)_2]$ were measured by the decrease in area of the 1988 $cm^{-1}$ band of $Li[RhI_2(CO)_2]$ with time. The reaction constants in FIGS. 2-4 are the methyl iodide oxidative addition step.

Figure 2:
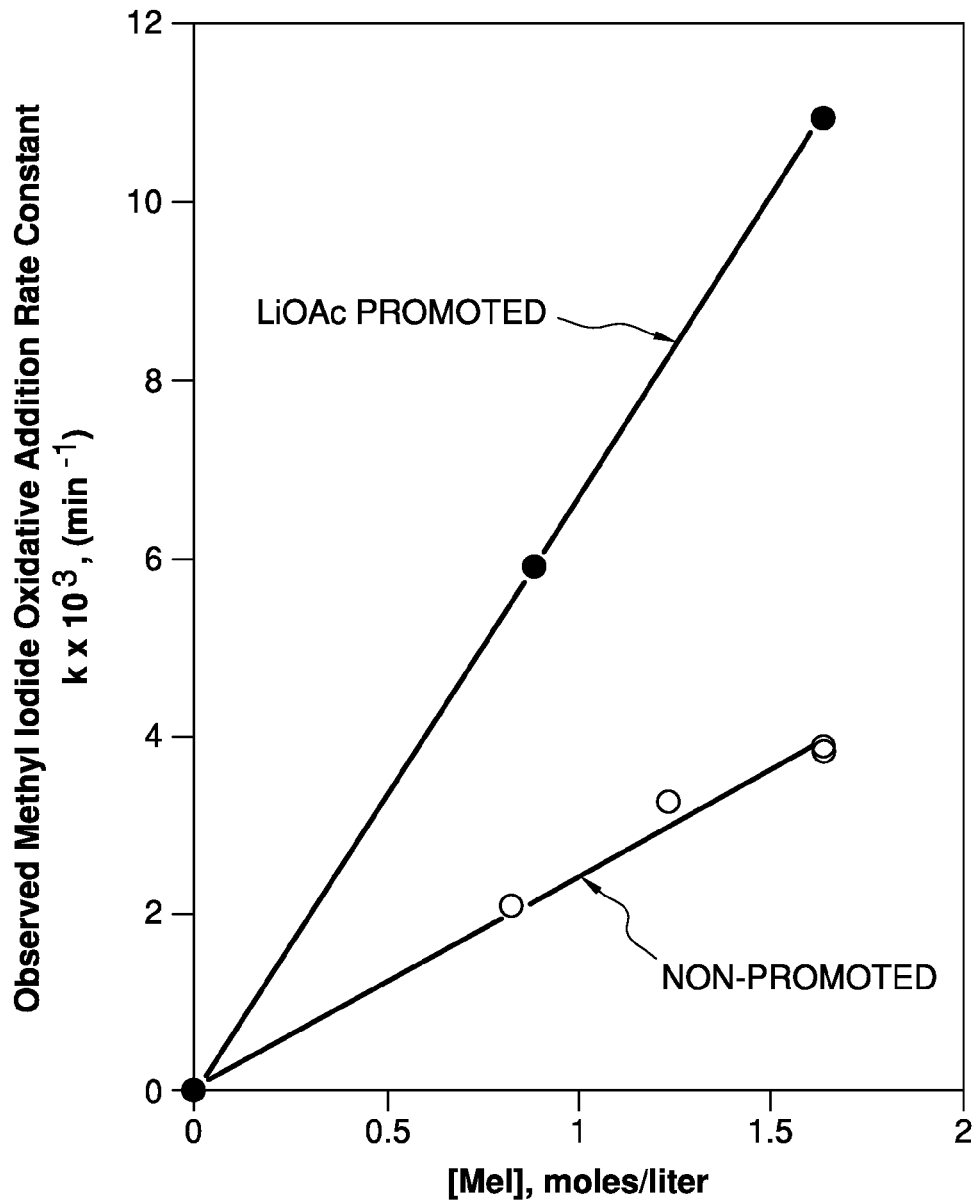
FIG. 2 is a graph of the promoting effect of lithium acetate on methyl iodide oxidative addition rate constant based on methyl iodide concentration.
Figure 3:
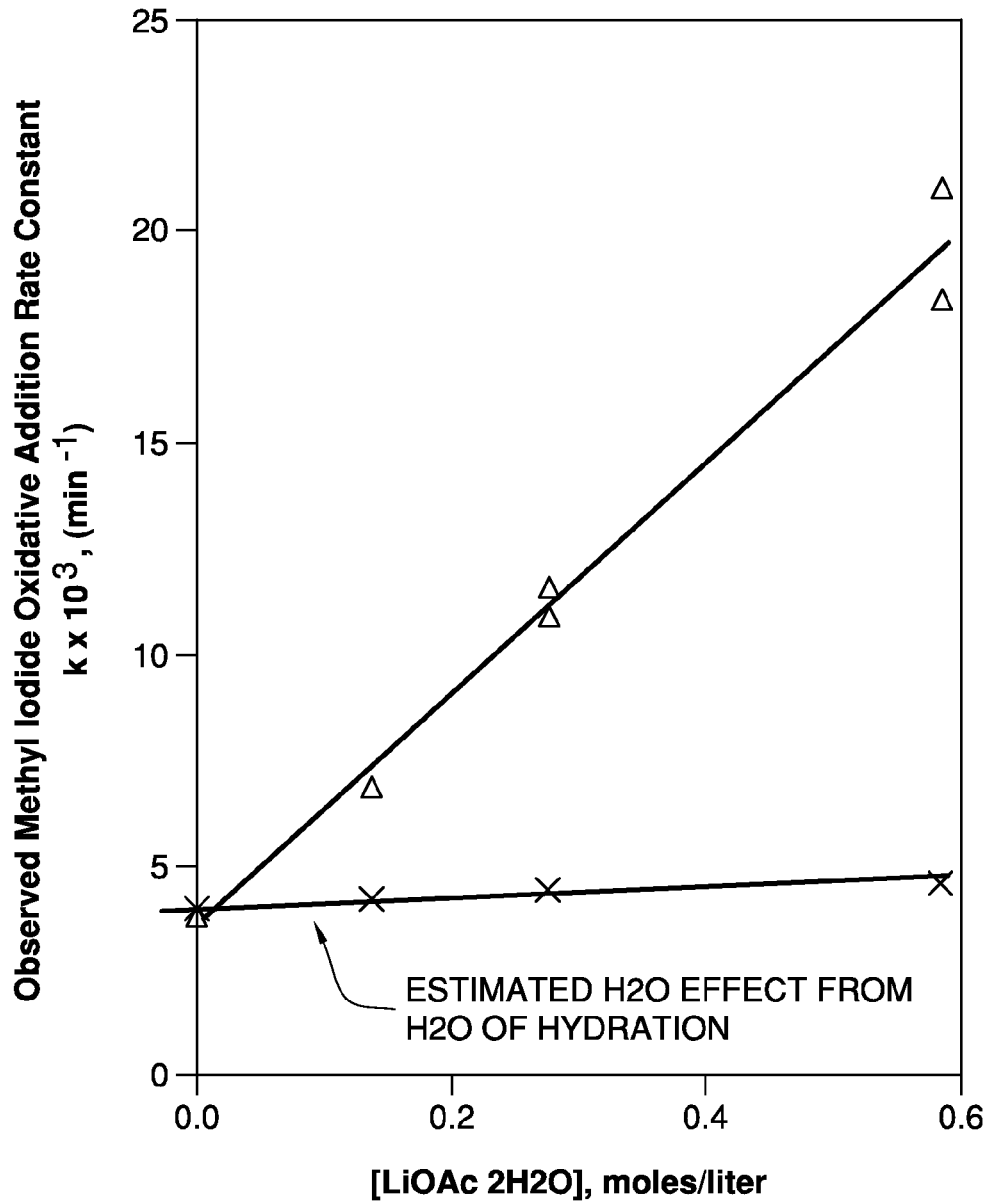
FIG. 3 is a graph of the promoting effect of lithium acetate on methyl iodide oxidative addition rate constant based on lithium acetate dehydrate concentration.

FIG. 2 shows the promotional effect of lithium acetate on reaction rates in mixture having 2 wt. % water and acetic acid. The closed circles indicate the promotion of the methyl iodide oxidative addition step in the presence of lithium acetate. FIG. 3 shows the linear increase of observed rates with the increasing lithium acetate concentrations, indicative of first order promotional effects of reaction between methyl iodide and $Li[RhI_2(CO)_2]$. The source of lithium acetate used in this example was in the dihydrated $Li[CH_3CO_2].2H_2O$. The promotion effect of the two moles of water per mole of lithium acetate was estimated from the similar kinetic measurement of water, and the estimate is shown in the lower curve in FIG. 3. As is apparent from FIG. 3, the effect on a molar basis of water is negligible. A non-zero intercept in FIG. 3 shows that lithium acetate is not required for the MeI—Rh(I) reaction to occur, but the lithium acetate does give considerable promotional effect even at low concentrations.

Addition of lithium acetate to methyl iodide-free solutions of $Li[RhI_2(CO)_2]$ did not detectibly alter the IR spectrum of the Rh(I) complex. Also the addition of lithium acetate did not cause observable chemical reactions or decomposition after several hours. Gas chromatograph showed that lithium acetate does not react with methyl iodide to produce methyl acetate and lithium iodide on the 2-3 hour timescale of a room temperature kinetic run.

Figure 4:
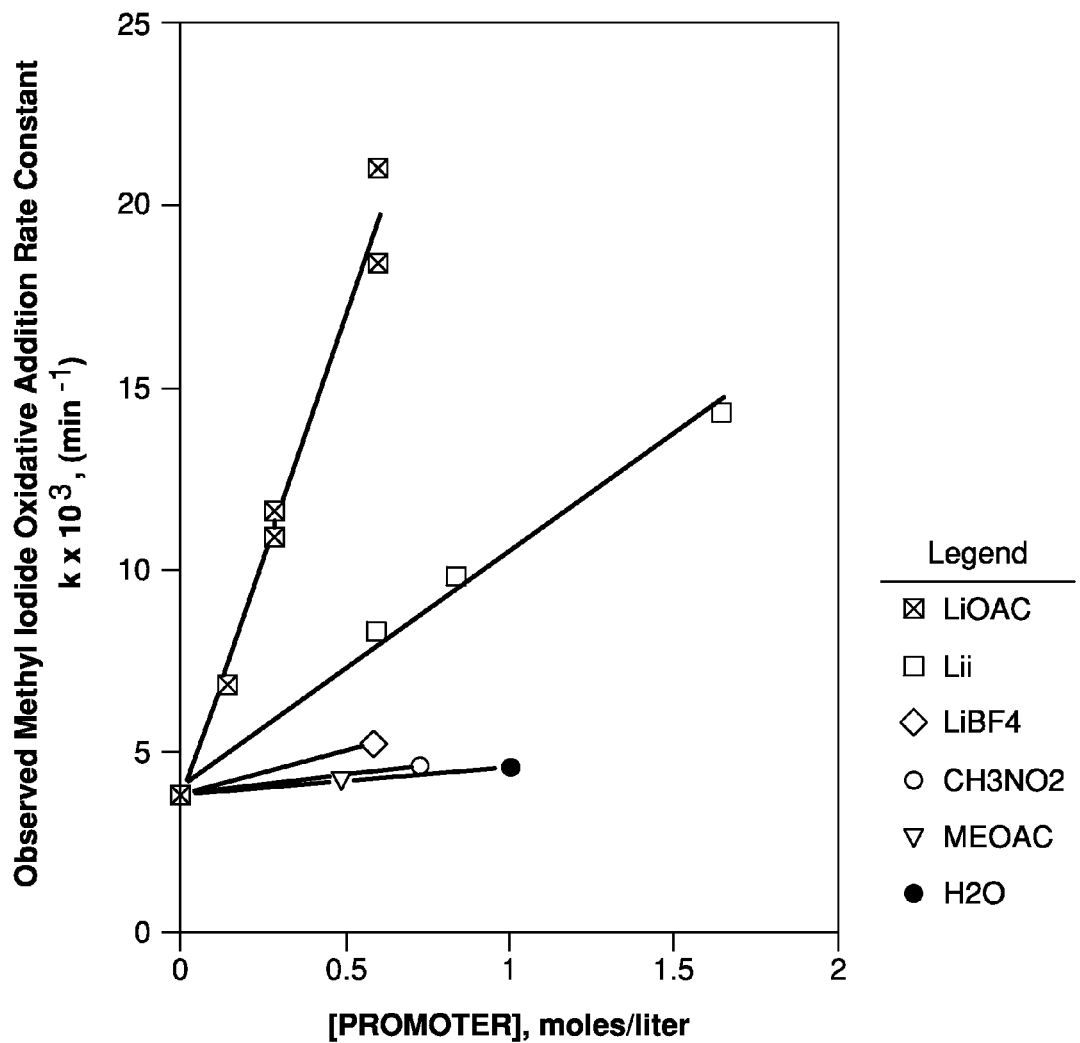
FIG. 4 is a graph comparing the promoting effect of several promoters on methyl iodide oxidative addition rate constant based on promoter concentration.

As shown in FIG. 4, water, methyl acetate, nitromethane ($CH_3NO_2$), and lithium tetrafluoroborate ($Li[BF_4]$) were found to give only small increases in rate "per mole of additive," and the effects of each additive were similar. The additives change solvent "polarity" or "ionic strength," which only slightly effects the reaction of $[RhI_2(CO)_2]^-$ with methyl iodide. In contrast, to the small promotional effects of these other additives, lithium acetate strongly promoted the methyl iodide addition to $Li[RhI_2(CO)_2]$. Lithium acetate demonstrated a forty-three times promotional effect over water, implying that lithium acetate is a very strong promoter. Lithium iodide also promoted the methyl iodide addition, but slope of the lithium acetate curve in FIG. 4 is above four times that of lithium iodide.

What is claimed is:
1. A process for producing acetic acid comprising:
  carbonylating a reactant feed stream selected from the group consisting of methanol, methyl acetate, dimethyl ether, or mixtures thereof in a reactor in the presence of water, rhodium catalyst, iodide salt, and methyl iodide to form a reaction medium;

introducing a lithium compound into the reactor; and
maintaining a concentration of lithium acetate in the reaction medium from 0.3 to 0.7 wt. %, and the concentration of hydrogen iodide in the reaction medium from 0.1 to 1.3 wt. %;
wherein the concentration of the rhodium catalyst in the reaction medium is maintained from 300 to 3000 wppm, as rhodium, the concentration of water in the reaction medium is maintained from 0.1 to 4.1 wt. %, and the concentration of methyl acetate in the reaction medium is maintained from 0.6 to 4.1 wt. %.

2. The process of claim 1, wherein the lithium compound is selected from the group consisting of lithium acetates, lithium carboxylates, lithium carbonates, lithium hydroxides, and mixtures thereof.

3. The process of claim 1, wherein the concentration of methyl iodide in the reaction medium is maintained from 4 to 13.9 wt. %, and preferably from 4 to 13 wt. %.

4. The process of claim 1, wherein the concentration of iodide salt in the reaction medium is maintained from 2 to 20 wt. %.

5. The process of claim 4, wherein the concentration of iodide salt in the reaction medium is maintained from 8 to 14 wt. %.

6. The process of claim 1, wherein is the production rate of acetic acid is from 5 mol/L·h to 50 mol/L·h.

7. The process of claim 1, wherein the reaction is conducted while maintaining a carbon monoxide partial pressure from 2 to 30 atm and a hydrogen partial pressure in the reactor that is less than or equal to 0.04 atm.

8. The process of claim 1, wherein the concentration of methyl acetate in the reaction medium is greater than or equal to the concentration of the lithium acetate.

9. The process of claim 1, wherein the reaction is conducted at a temperature from 150° C. to 250° C. and at a pressure from 15 to 40 atm.

10. The process of claim 1, wherein the weight ratio of iodide salt to the lithium compound is greater than or equal to 5:1.

11. The process of claim 1, wherein in the reaction medium, the concentration of lithium acetate is maintained from 0.3 to 0.6 wt. %, the concentration of the rhodium catalyst is maintained from 800 to 3000 wppm, the concentration of water is maintained from 0.1 to 3.1 wt. %, the concentration of methyl acetate is maintained from 1.8 to 3.9 wt. %, and the concentration of hydrogen iodide is maintained from 0.1 to 1 wt. %.

12. The process of claim 1, wherein in the reaction medium, the concentration of lithium acetate is maintained from 0.35 to 0.55 wt. %, the concentration of the rhodium catalyst is maintained from 900 to 1500 wppm, the concentration of water is maintained from 0.5 to 2.8 wt. %, the concentration of methyl acetate is maintained from 2 to 3.5 wt. %, and the concentration of hydrogen iodide is maintained from 0.2 to 0.8 wt. % in the reaction medium.

13. The process of claim 1, wherein the production rate of acetic acid is from 10 mol/L·h to 40 mol/L·h and wherein in the reaction medium, the concentration of lithium acetate is maintained from 0.3 to 0.6 wt. %, the concentration of the rhodium catalyst is maintained from 800 to 3000 wppm, the concentration of water is maintained from 0.1 to 3.1 wt. %, the concentration of methyl acetate is maintained from 1.8 to 3.9 wt. %, and the concentration of hydrogen iodide is maintained from 0.1 to 1 wt. %.

14. The process of claim 1, wherein the production rate of acetic acid is from 15 mol/L·h to 35 mol/L·h and wherein in the reaction medium, the concentration of lithium acetate is maintained from 0.35 to 0.55 wt. %, the concentration of the rhodium catalyst is maintained from 900 to 1500 wppm, the concentration of water is maintained from 0.5 to 2.8 wt. %, the concentration of methyl acetate is maintained from 2 to 3.5 wt. %, and the concentration of hydrogen iodide is maintained from 0.2 to 0.8 wt. % in the reaction medium.

15. The process of claim 1, wherein the concentration of lithium acetate in the reaction medium is maintained from 0.3 to 0.6 wt. %.

16. The process of claim 1, wherein the concentration of hydrogen iodide in the reaction medium is maintained from 0.1 to 1 wt. %, and preferably from 0.2 to 0.8 wt. %.

17. A process for producing acetic acid comprising:
carbonylating a reactant feed stream selected from the group consisting of methanol, methyl acetate, dimethyl ether, or mixtures thereof in a reactor in the presence of water, rhodium catalyst, iodide salt, and
methyl iodide to form a reaction medium, wherein the concentration of water in the reaction medium is maintained from 0.1 to 4.1 wt. %;
introducing a lithium compound into the reactor;
maintaining a concentration of lithium acetate in the reaction medium from 0.3 to 0.7 wt. %;
venting a gaseous stream from the reactor, wherein the gaseous stream comprises hydrogen iodide in an amount of less than or equal to 1 wt. %, and
recovering acetic acid from the reaction medium.

18. The process of claim 17, wherein the gaseous stream comprises hydrogen iodide in an amount from 0.001 to 1 wt. %.

19. The process of claim 17, wherein the concentration of the rhodium catalyst in the reaction medium is maintained from 300 to 3000 wppm, as rhodium, the concentration of water in the reaction medium is maintained from 0.1 to 4.1 wt. %, and the concentration of methyl acetate in the reaction medium is maintained from 0.6 to 4.1 wt. %.

20. The process of claim 17, further comprising scrubbing the gaseous stream to remove hydrogen iodide from a purge stream.

* * * * *